United States Patent
Null et al.

(10) Patent No.: US 7,572,264 B2
(45) Date of Patent: Aug. 11, 2009

(54) DRIVER INSTRUMENT FOR USE IN A SURGICAL APPLICATION

(75) Inventors: Barry Null, Olive Branch, TN (US); Wilder Companioni, Cordova, TN (US)

(73) Assignee: Warsaw Orthopedic, Inc.

( * ) Notice: Subject to any disclaimer, the term of this patent is extended or adjusted under 35 U.S.C. 154(b) by 116 days.

(21) Appl. No.: 11/168,121

(22) Filed: Jun. 28, 2005

(65) Prior Publication Data

US 2007/0005077 A1    Jan. 4, 2007

(51) Int. Cl.
*A61B 17/58* (2006.01)
(52) U.S. Cl. .................................... 606/104
(58) Field of Classification Search ............ 606/79–81, 606/86, 104; 81/452–458
See application file for complete search history.

(56) References Cited

U.S. PATENT DOCUMENTS

| | | | |
|---|---|---|---|
| 2,248,054 A * | 7/1941 | Becker | 81/457 |
| 2,952,285 A * | 9/1960 | Roosli | 81/453 |
| 3,498,351 A | 3/1970 | Edwards et al. | |
| 3,604,487 A | 9/1971 | Gilbert | |
| 4,581,963 A | 4/1986 | Kim | |
| 4,704,929 A | 11/1987 | Osada | |
| 4,763,548 A * | 8/1988 | Leibinger et al. | 81/453 |
| 4,963,144 A | 10/1990 | Huene | |
| 5,052,253 A | 10/1991 | Lin | |
| 5,139,499 A | 8/1992 | Small et al. | |
| 5,431,660 A | 7/1995 | Burke | |
| 5,484,440 A | 1/1996 | Allard | |
| 5,520,696 A | 5/1996 | Wenstrom, Jr. | |
| 5,649,931 A | 7/1997 | Bryant et al. | |
| 5,667,513 A * | 9/1997 | Torrie et al. | 606/104 |
| 6,132,435 A | 10/2000 | Young | |
| 6,189,422 B1 | 2/2001 | Stihl | |
| 6,273,893 B1 * | 8/2001 | McAllen et al. | 606/104 |
| 6,402,759 B1 | 6/2002 | Strong et al. | |
| 6,415,693 B1 | 7/2002 | Simon et al. | |
| 6,857,343 B1 | 2/2005 | Easterbrooks et al. | |
| 2003/0125750 A1 | 7/2003 | Zwirnmann et al. | |
| 2003/0158555 A1 * | 8/2003 | Sanders et al. | 606/73 |

* cited by examiner

*Primary Examiner*—Eduardo C Robert
*Assistant Examiner*—Michael J Araj (57) ABSTRACT

A surgical instrument for driving a threaded member into a substrate generally includes a drive shaft, a support member and a biasing member. The drive shaft is configured for releasable engagement with the threaded member. The drive shaft is axially coupled with the support member in a manner allowing relative axial displacement therebetween, with the drive shaft rotatably coupled with the support member. The biasing member is coupled between the support member and the drive shaft to transmit an axial force from the support member to the drive shaft as the threaded member is driven into the substrate, and with the axial force being limited as a distal end of the support member is engaged against a surface adjacent the substrate to correspondingly limit an axial force exerted onto the threaded member by the drive shaft to facilitate rotational disengagement of the drive shaft from the threaded member.

36 Claims, 5 Drawing Sheets

DRIVER INSTRUMENT FOR USE IN A SURGICAL APPLICATION

FIELD OF THE INVENTION

The present invention relates generally to the field of surgical instrumentation, and more particularly relates to a surgical instrument for driving a threaded member into a substrate.

BACKGROUND

Various types of fasteners are used to engage implants and other devices to bone. In the spinal field, bone screws are commonly used to attach plates, rods and other types of implants and devices to one or more vertebrae. In some instances, a relatively high degree of precision is required to engage the bone screws in the proper position and orientation relative to the spinal column. Additionally, in the past, the surgeon had to manipulate tissue and/or other anatomical structures while holding the bone screw in position with one hand, while at the same time grasping and rotating a screwdriver with the other hand to drive the screw into engagement with vertebral bone. In some instances, the bone screw may be held in position via the use of a holding instrument that is manipulated in one hand while grasping and manipulating a screwdriver with the other hand. The non-positive engagement between the holding instrument, the screwdriver and the bone screw may lead to instability, thereby making the process of driving the bone screw into bone more difficult, awkward and time consuming. Furthermore, there is also a risk of applying excess torque to the bone screw and potentially breaking the screw and/or stripping out the threads formed in the bone.

Thus, there remains a need for an improved surgical instrument for driving a threaded member into a substrate. The present invention satisfies this need and provides other benefits and advantages in a novel and unobvious manner.

SUMMARY

The present invention relates generally to a surgical instrument for driving a threaded member into a substrate. While the actual nature of the invention covered herein can only be determined with reference to the claims appended hereto, certain forms of the invention that are characteristic of the preferred embodiments disclosed herein are described briefly as follows.

In one form of the present invention, a surgical instrument is provided which generally includes a drive shaft, a support member and a biasing member. The drive shaft extends generally along a longitudinal axis and includes a distal end portion configured for releasable engagement with a threaded member. The drive shaft is axially coupled with the support member in a manner allowing relative axial displacement therebetween, and is rotatably coupled with the support member such that rotation of the support member correspondingly rotates the drive shaft. The biasing member is configured to transmit an axial force from the support member to the drive shaft as the threaded member is driven into the substrate, with the axial force being limited as a distal end of the support member is engaged against a surface adjacent the substrate to correspondingly limit an axial force exerted onto the threaded member by the drive shaft to facilitate rotational disengagement of the drive shaft from the threaded member.

In another form of the present invention, a surgical instrument is provided which generally includes a drive shaft, an outer sleeve and a biasing member. The drive shaft extends generally along a longitudinal axis and includes a distal end portion having a distal end and defining a first axial passage extending from the distal end, with the first axial passage being sized and shaped to receive a head portion of a threaded member therein to releasably engage the drive shaft with the threaded member. The outer sleeve defines a second axial passage sized to receive the drive shaft therein and includes a distal end positioned adjacent the distal end portion of the drive shaft. The drive shaft is axially coupled with the outer sleeve in a manner allowing axial displacement of the drive shaft along the second axial passage, and the drive shaft is rotatably coupled with the outer sleeve such that rotation of the outer sleeve correspondingly rotates the drive shaft. The biasing member is coupled between the outer sleeve and the drive shaft and is configured to transmit an axial force from the outer sleeve to the drive shaft as the threaded member is driven into the substrate, with the axial force being limited as a distal end of the outer sleeve is engaged against a surface adjacent the substrate to correspondingly limit an axial force exerted onto the threaded member by the drive shaft to facilitate rotational disengagement of the drive shaft from the head portion of the threaded member.

In another form of the present invention, a surgical instrument is provided which generally includes a drive shaft extending along a longitudinal axis and having a distal end portion configured for releasable engagement with a threaded member. The distal end portion has a distal end and defines a passage extending from the distal end generally along the longitudinal axis. The passage is sized and shaped to receive a head portion of the threaded member therein and defines a tapered portion tapering outwardly toward the distal end to facilitate rotational disengagement of the drive shaft from the head portion of the threaded member.

It is one object of the present invention to provide an improved surgical instrument for driving a threaded member into a substrate. Further objects, features, advantages, benefits, and aspects of the present invention will become apparent from the drawings and description contained herein.

DESCRIPTION OF THE PREFERRED EMBODIMENTS

For the purposes of promoting an understanding of the principles of the invention, reference will now be made to the embodiments illustrated in the drawings and specific language will be used to describe the same. It will nevertheless be understood that no limitation of the scope of the invention is hereby intended, and that alterations and further modifications to the illustrated devices and/or further applications of the principles of the invention as illustrated herein are contemplated as would normally occur to one skilled in the art to which the invention relates.

Figure 1:
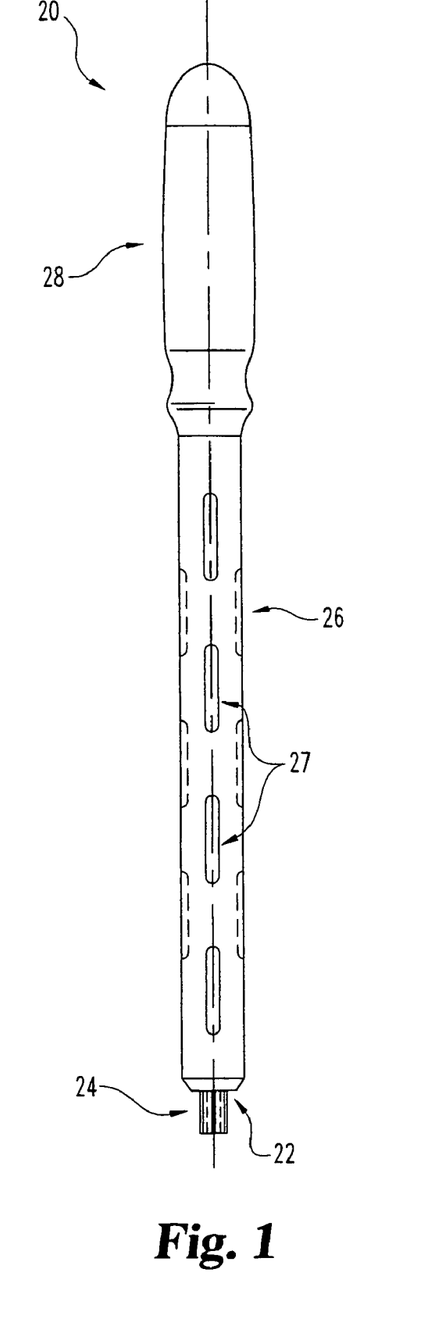
FIG. 1 is a driver instrument according to one form of the present invention for driving a threaded member into bone.
Figure 2:
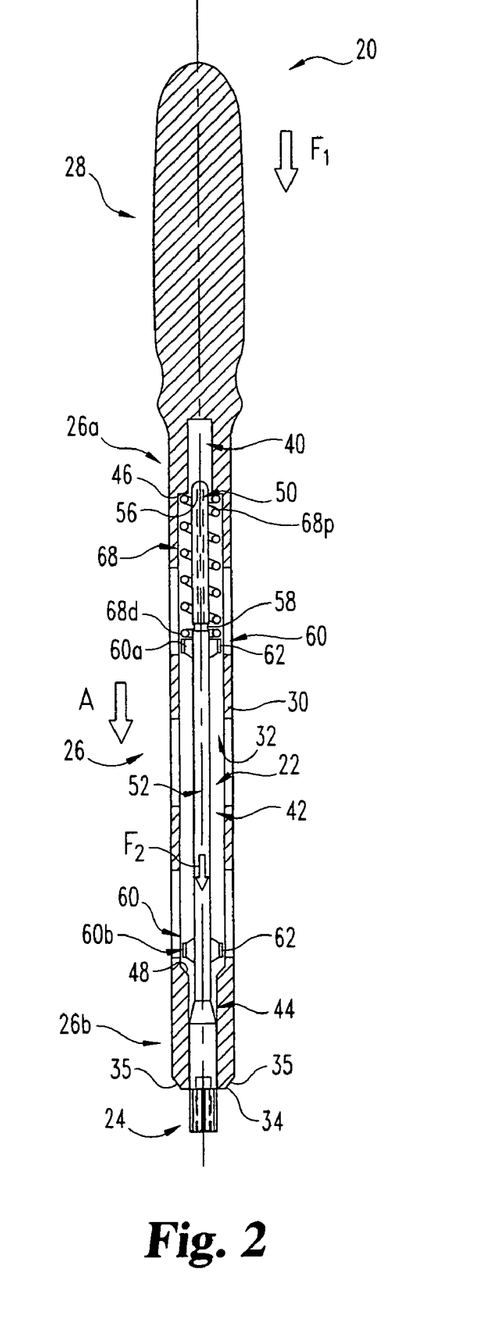
FIG. 2 is partial cross sectional side view of the driver instrument shown in FIG. 1.

Referring to FIGS. 1 and 2, shown therein is a driver instrument 20 according to one form of the present invention. In one embodiment, the driver instrument 20 extends generally along a longitudinal axis L and is comprised of a drive shaft 22 including a distal end portion 24 configured for selective and releasable engagement with a threaded member, a support member 26 extending along the drive shaft 22, and a handle 28 extending from the support member 26. In the illustrated embodiment, the support member 26 comprises a sleeve, with the drive shaft 22 positioned within the sleeve 26 and with the handle 28 attached to a proximal end portion of the sleeve 26. As will be discussed in greater detail below, the driver instrument 20 is configured such that the inner drive shaft 22 is axially displaceable within the outer sleeve 26, but is rotatably engaged with the outer sleeve 26 such that rotation of the outer sleeve 26 generally about the longitudinal axis L correspondingly rotates the inner drive shaft 22. In one embodiment of the invention, the components of the driver instrument 20 are formed of stainless steel or titanium materials. However, it should be understood that other materials are also contemplated including, for example, metallic alloy materials, polymeric materials, reinforced composite materials, or any other suitable material that would occur to one of ordinary skill in the art.

In one embodiment of the invention, the driver instrument 20 is used in association with a threaded member 100 (FIGS. 8-10) to drive the threaded member 100 into engagement with a substrate, such as, for example, bone. In one aspect of the invention, the driver instrument 20 includes one or more elements or features that limit or regulate the amount of rotational torque and/or axial force that can be applied to the threaded member 100, the details of which will be discussed in greater detail below. In the illustrated embodiment, the threaded member 100 comprises fastener. In a specific embodiment, the threaded fastener comprises a bone screw configured for engagement with vertebral bone. However, it should be understood that other type and configurations of threaded members are also contemplated for use in association with the present invention such as, for example, other types of fasteners including bolts or pins, or a tapping device having external threads configured to cut internal threads along a passage in bone. Additionally, it should also be understood that the driver instrument 20 may be used to drive the bone screw 100 into substrates other than bone including, for example, spinal implants or other surgical implants or devices. In a specific embodiment of the invention, the bone screw 100 is formed of a polymeric material. However, other materials are also contemplated including, for example, titanium and stainless steel materials, or any other biocompatible material that would occur to one of ordinary skill in the art.

Figure 8:
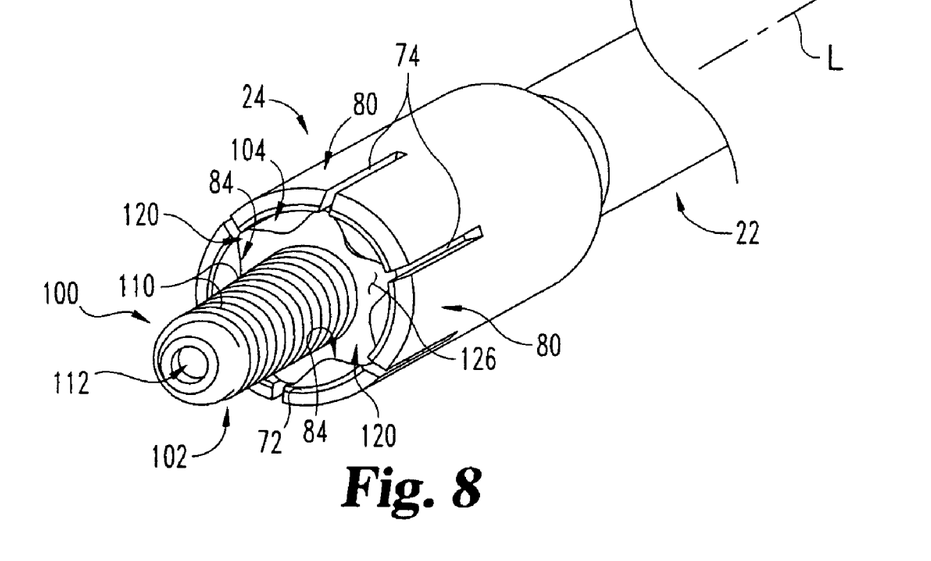
FIG. 8 is a perspective view of a threaded fastener engaged within the distal end portion of the inner drive shaft shown in FIG. 5.
Figure 9:
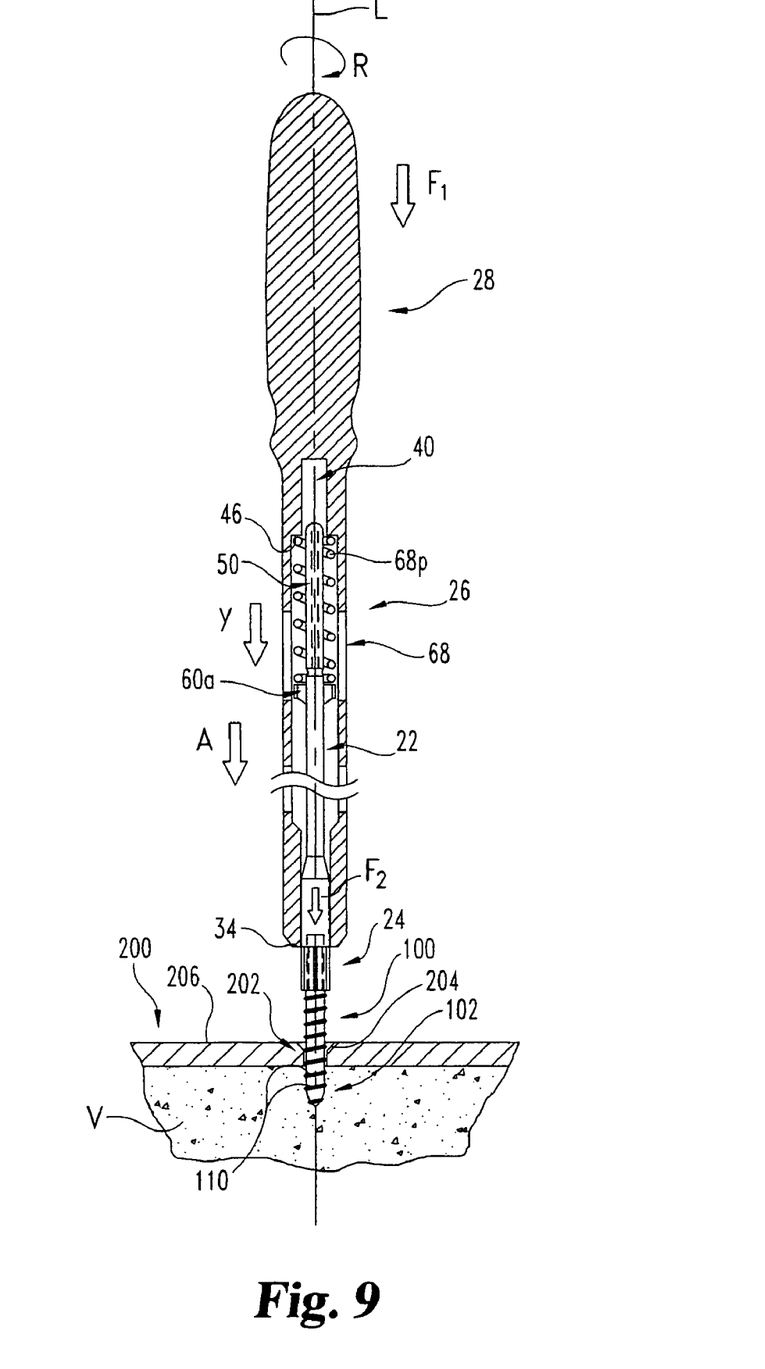
FIG. 9 is partial cross sectional side view of the driver instrument shown in FIG. 1, with the threaded fastener shown in FIG. 8 being driven into a vertebra.
Figure 10:
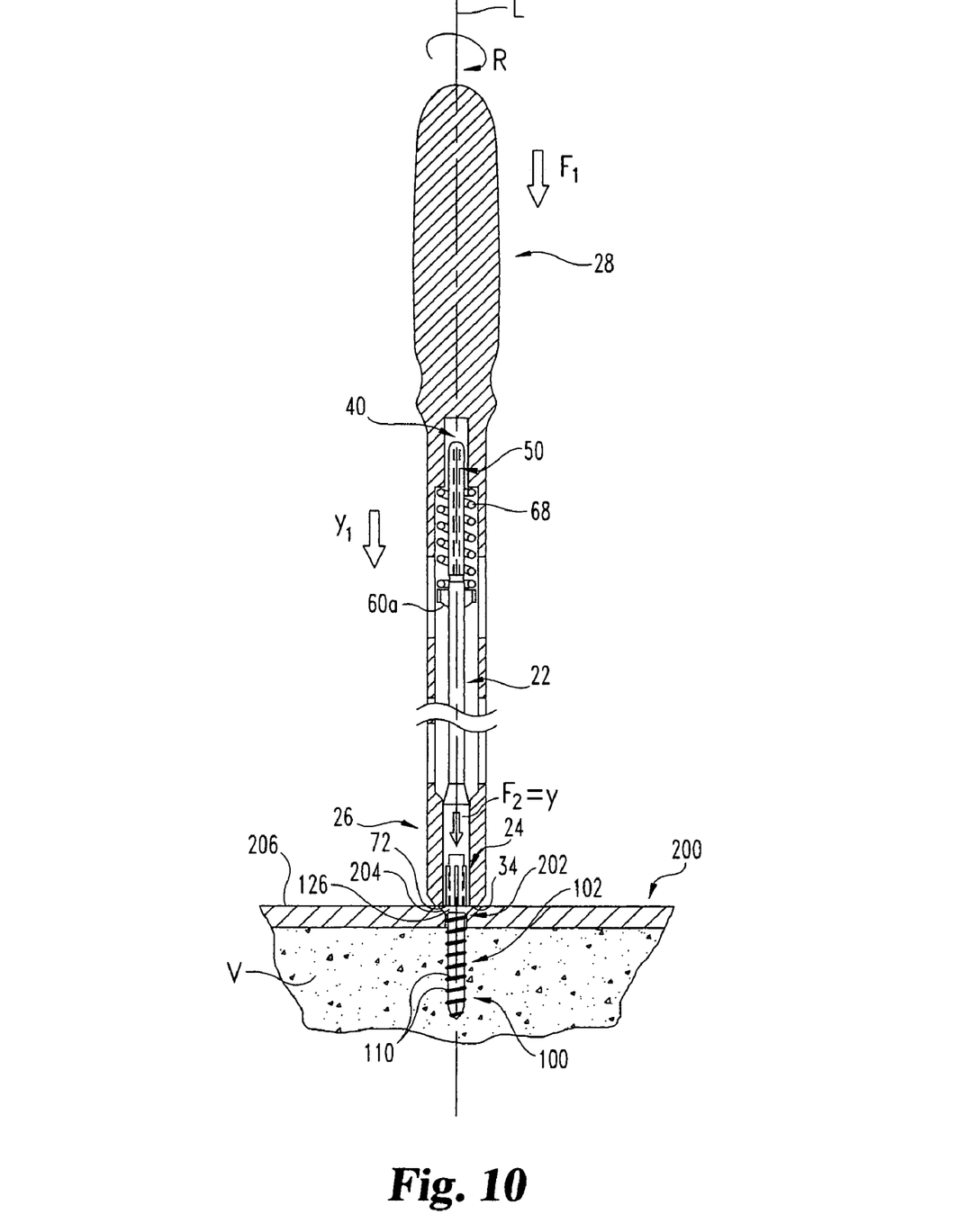
FIG. 10 is partial cross sectional side view of the driver instrument shown in FIG. 1, with the threaded fastener fully driven into the vertebra.

As shown in FIGS. 8-10, the bone screw 100 includes a threaded shank portion 102 and a head portion 104 extending therefrom. In the illustrated embodiment, the threaded shank portion 102 includes external threads 110 adapted for engagement with cancellous bone, with the distal end of the threaded shank portion 102 defining a hollowed out area 112. However, other types and configurations of the threaded shank portion 102 are also contemplated. In one aspect of the invention, the head portion 104 is shaped for selective and releasable engagement within a correspondingly shaped recess formed in the distal end portion 24 of the drive shaft 22. In one embodiment, the head portion 104 has a non-circular shape. In the illustrated embodiment, the head portion 104 has a splined configuration defining a Torx™ style shape having six rounded projections 120 extending radially outward relative to the longitudinal axis L. However, it should be understood that the head portion 104 may define any number of projections 120, including a single projection, two to five projections, or seven or more projections. It should also be understood that other shapes and configurations of the head portion 104 are also contemplated as falling within the scope of the present invention including, for example, a star shape, a cross shape, a rectangular shape, a hexagonal shape, a triangular shape, other polygonal shapes, or any other suitable shape or configuration that would occur to one of ordinary skill in the art.

In one embodiment of the invention, the head portion 104 also defines a tool-receiving recess (not shown) that opens onto an upper surface of the head portion 104. In one embodiment, the tool-receiving recess has a hexagonal shape that is sized and configured to receive a correspondingly shaped distal end portion of an instrument therein to facilitate unthreading of the bone screw 100 from the substrate. However, it should be understood that other suitable shapes and configuration of the tool-receiving recess are also contemplated. Additionally, in the illustrated embodiment, the screw head portion 104 defines a tapered or conical-shaped lower surface 126, the purpose of which will be discussed below.

As shown in FIG. 2, the outer sleeve 26 includes a proximal end portion 26a, a distal end portion 26b, and an outer wall 30 defining an axial passage 32 extending generally along the longitudinal axis L and opening onto a distal end 34 of the outer wall 30. The axial passage 32 includes a proximal portion 40, a central portion 42 and a distal portion 44. The proximal passage portion 40 is sized and shaped to receive a proximal end portion of the drive shaft 22 therein, the details of which will be discussed below. The proximal passage portion 40 also has a somewhat smaller cross section than the central passage portion 42 so as to define a distally-facing shoulder 46. Similarly, the distal passage portion 44 has a somewhat smaller cross section than the central passage portion 42 so as to define a proximally-facing shoulder 48. Additionally, the outer wall 30 of the sleeve 26 near the distal end 34 defines an outer chamfer 35 to minimize trauma or injury to adjacent tissue. Alternatively, the distal end 34 may be rounded to minimize trauma or injury to adjacent tissue.

As shown in FIG. 1, in one embodiment of the invention, the outer sleeve 26 defines a number of openings 27 extending through the outer wall 30 and communicating with the axial passage 32. One purpose of the openings 27 is to provide for adequate sterilization of the components positioned internal to the sleeve 26 (e.g., the drive shaft 22 and the biasing member 68). Although the openings 27 are illustrated as having an elongated slot configuration extending generally along the longitudinal axis L, it should be understood that other types and configuration of openings are also contemplated. It should also be understood that the openings 27 can be provided in various sizes and at different positions along the outer sleeve 22. In the illustrated embodiment, the handle 28 is formed integral with the outer sleeve 26. However, other embodiments are also contemplated where the handle 28 and the outer sleeve 26 are formed separately and assembled together to form an integrated structure. In the illustrated embodiment, the handle 28 is configured as a conventional screwdriver handle. However, other types and configurations of handles are also contemplated as would occur to one of ordinary skill in the art.

Figure 3:
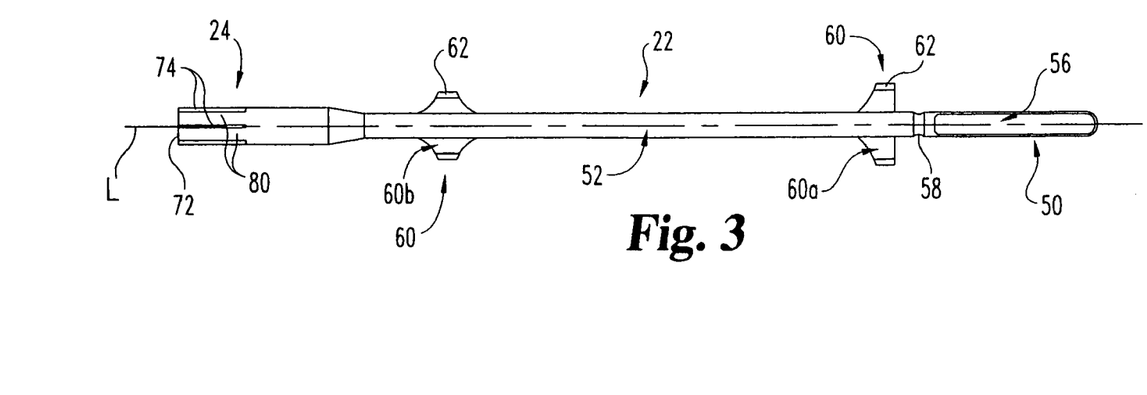
FIG. 3 is a side view of an inner drive shaft according to one embodiment of the present invention for use in association with the driver instrument shown in FIG. 1.
Figure 4:
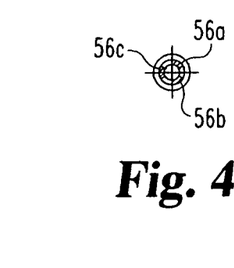
FIG. 4 is an end view of the proximal end portion of the inner drive shaft shown in FIG. 3.

Referring collectively to FIGS. 2-4, the inner drive shaft 22 includes a distal end portion 24 configured for selective and releasable engagement with a bone screw 100. In the illustrated embodiment, the drive shaft 22 further includes a proximal end portion 50 that is sized and configured for receipt within the proximal portion 40 of the passage 32 in the outer sleeve 26, and a central body portion 52 extending between the proximal shaft portion 50 and the distal end portion 24. In a further aspect of the invention, the proximal passage portion 40 and the proximal shaft portion 50 are configured in a manner which permits the drive shaft 22 to be axially displaced relative to the outer sleeve 26, but which substantially prohibits or prevents rotational displacement of the outer sleeve 26 relative to drive shaft 22. Accordingly, a torsional force may be transmitted from the handle 28 to the distal end portion 24 of the drive shaft 22 (via the outer sleeve 26) and onto the head portion 104 of the bone screw 100, the details of which will be discussed below.

In the illustrated embodiment of the invention, the proximal shaft portion 50 has a non-circular shape that is sized and shaped for positioning within the proximal passage portion 40. In one embodiment, the proximal shaft portion 50 defines a number of truncated or flatted areas 56. In the illustrated embodiment, the drive shaft 22 defines three truncated or flatted areas 56a, 56b, 56c that provide the proximal shaft portion 50 with a generally triangular-shaped configuration, with the proximal passage portion 40 having a correspondingly shaped configuration to slidably receive the proximal shaft portion 50 therein. As should be appreciated, the truncated or flatted areas 56a, 56b, 56c of the proximal shaft portion 50 are allowed to be axially displaced along corresponding flat or planar surfaces (not shown) defined within the proximal passage portion 40, but which engage one another to substantially prevent relative rotation between the outer sleeve 26 and the drive shaft 22.

Although a specific shape and configuration of the proximal passage portion 40 and the proximal shaft portion 50 have been illustrated and described herein, it should be understood that other shapes and configurations of the proximal shaft portion 50 that are sized and configured for receipt within the proximal passage portion 40 in a manner which permits relative axial displacement between the drive shaft 22 and the outer sleeve 26, but which substantially prohibits or prevents relative rotational displacement therebetween, are also contemplated as falling within the scope of the present invention. For example, either the proximal passage portion 40 and/or the proximal shaft portion 50 may be provided with other shapes and configurations such as, for example, a hexagonal shape, a Torx™ shape, a star shape, a cross shape, a rectangular shape, other polygonal shapes, or any other suitable shape or configuration that would occur to one of ordinary skill in the art.

In another embodiment of the invention, either the proximal passage portion 40 or the proximal shaft portion 50 may be provided with one or more axially-extending splines that are slidably received within corresponding axially-extending grooves formed along the other of the proximal passage portion 40 and the proximal shaft portion 50. It should also be understood that other portions or elements associated with the drive shaft 22 may be engaged with the outer sleeve 26 in a manner which permits relative axial displacement between the drive shaft 22 and the outer sleeve 26 while substantially prohibiting or preventing relative rotational displacement therebetween. For example, the drive shaft 22 may be provided with one or more projections extending transversely from a portion of the drive shaft and which are correspondingly positioned within axially-extending grooves formed along an inner surface of the outer sleeve 26. Alternatively, the outer sleeve 26 may be provided with one or more projections extending transversely from an inner surface of the wall 30 and which are correspondingly positioned within axially-extending grooves formed along an outer surface of the drive shaft 22.

In order to stabilize and support the drive shaft 22 within the outer sleeve 26, the driver instrument 20 is provided with one or more support elements or guide structures 60. In the illustrated embodiment, the driver instrument 20 is provided with a pair of bearing elements 60a, 60b positioned adjacent opposite end portions of the central shaft portion 52. However, it should be understood that any number of bearing elements may be utilized, including a single bearing element or three or more bearing elements. In one embodiment, the bearing elements 60a, 60b include outwardly facing bearing surfaces 62 that are engaged along an inner surface of the sleeve wall 30 to provide lateral support to the drive shaft 22, which in turn substantially prevents side-to-side movement of the drive shaft 22 within the outer sleeve 26, while still allowing rotational displacement of the drive shaft 22 within the outer sleeve 26. The bearing elements 60a, 60b also function to guide the drive shaft 22 generally along the longitudinal axis L as the drive shaft 22 is axially displaced relative to the outer sleeve 26. As should be appreciated, the lower bearing element 60b is engageable against the proximally-facing shoulder 48 defined by the outer sleeve 26 to retain the drive shaft 22 within the outer sleeve 26. Although a specific type and configuration of the bearing elements 60a, 60b have been illustrated and described herein, it should be understood that other types and configurations of support elements or guide structures are also contemplated for use in association with the driver instrument 20 as would occur to one of ordinary skill in the art.

In a further aspect of the invention, the driver instrument 20 is provided with a biasing member 68 engaged between the drive shaft 22 and the outer sleeve 26. In the illustrated embodiment, the biasing member 68 comprises a coil spring extending about the proximal shaft portion 50 and positioned between the upper bearing element 60a associated with the drive shaft 22 and the distally-facing shoulder 46 defined by the outer sleeve 26. The drive shaft 22 defines an annular groove 58 positioned adjacent the distal-most coil $68_d$ of the coil spring 68. Although a specific type of spring member has been illustrated and described herein, it should be understood that other configurations of springs and other types of biasing members are also contemplated for use in association with the present invention. As will be discussed in further detail below, the coil spring 68 is compressed between the upper bearing element 60a and the distally-facing shoulder 46 as the outer sleeve 26 is axially displaced relative to the drive shaft 22 in the direction of arrow A. As should be appreciated, the amount of axial force y generated by the compressed coil spring 68 is equal to the spring constant k multiplied by the distance x that the spring is compressed (i.e., $y_{lbs}=k^* x_{in}$). As will also be discussed in further detail below, the spring-loaded drive shaft 22 limits the amount of axial force $F_2$ that is transmitted through the drive shaft 22 and onto the threaded fastener 100, regardless of the amount of axial force $F_1$ that is applied by the surgeon onto the handle 28 and transmitted through the outer sleeve 26.

Figure 5:
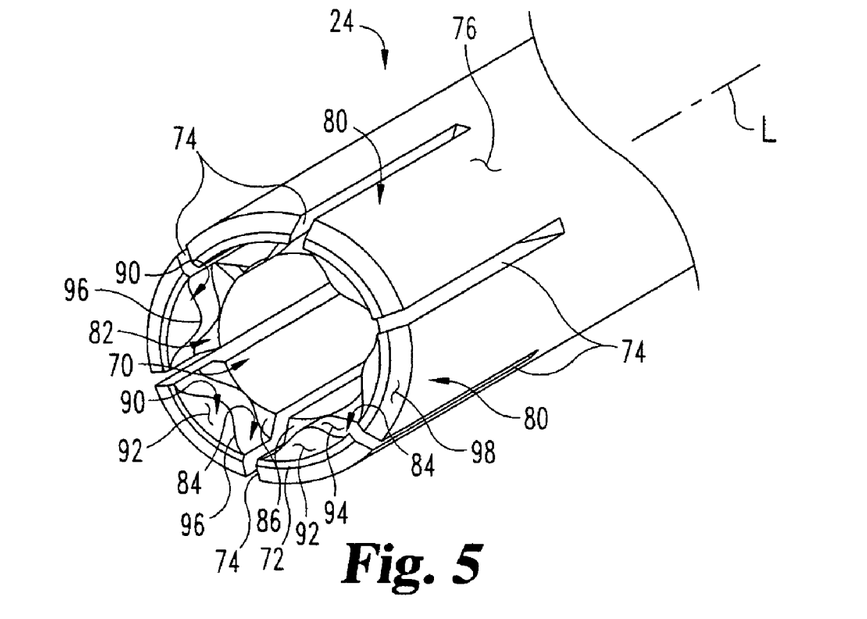
FIG. 5 is an enlarged perspective view of the distal end portion of the inner drive shaft shown in FIG. 3.
Figure 6:
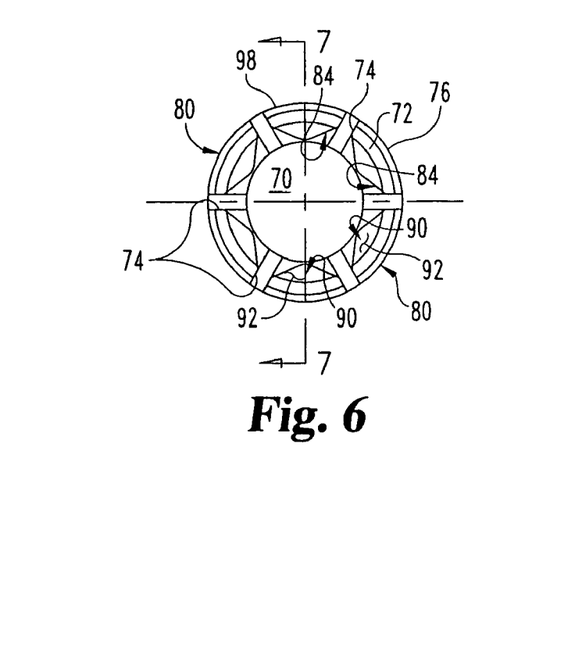
FIG. 6 is an end view of the distal end portion of the inner drive shaft shown in FIG. 5.
Figure 7:
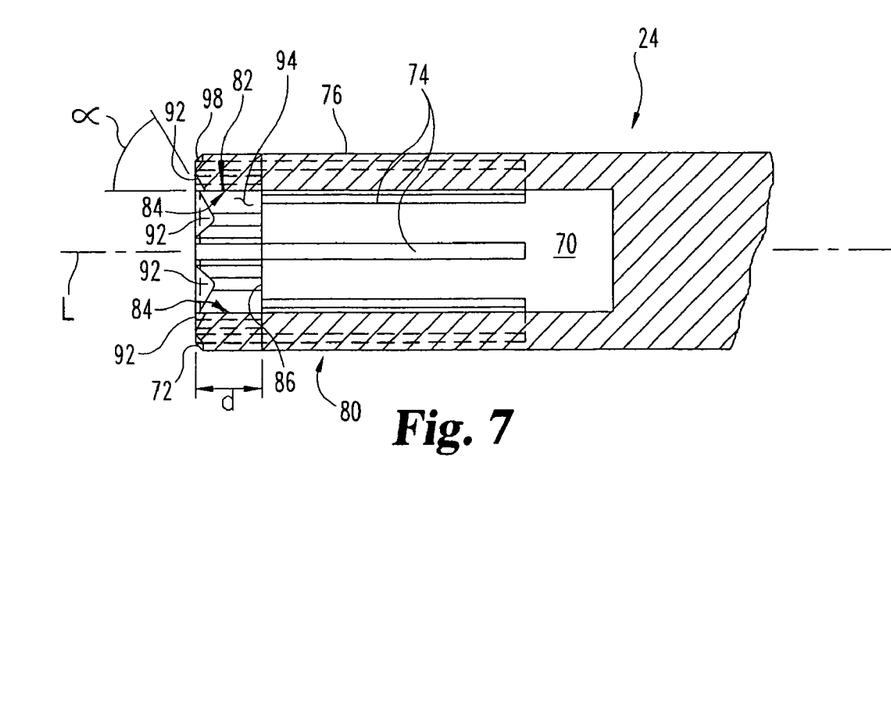
FIG. 7 is a cross sectional side view of the distal end portion of the inner drive shaft shown in FIG. 5, as taken along line 7-7 of FIG. 6.

Referring to FIGS. 5-7, shown therein are further details regarding the distal end portion 24 of the drive shaft 22 which is selectively and releasably engageable with the bone screw 100. The distal end potion 24 of the drive shaft 22 defines an axial passage 70 extending generally along the longitudinal axis L and opening onto a distal end 72 of the drive shaft 22. In another aspect of the present invention, the distal end portion 24 is configured to be flexibly and resiliently deformed in a manner that facilitates selective engagement and disengagement of the distal end portion 24 from the head portion 104 of the bone screw 100. In the illustrated embodiment, the distal end portion 24 defines a number of slots or slits 74 extending generally along the longitudinal axis L and communicating between the external surface 76 of the distal end portion 24 and the axial passage 70. The axially-extending slots 74 divide the distal end portion 24 into a number of axially-extending fingers or arms 80 that are configured to be flexibly and resiliently deflected in directions substantially normal to the longitudinal axis L (e.g., displaced away from and toward the longitudinal axis L in a generally radial direction). As will be discussed below, the axially-extending slots 74 facilitate outward deflection of the arms 80 to accept the head portion 104 of the bone screw 100 and to facilitate resilient inward deflection of the arms 80 to grip the head portion 104 to maintain engagement between the drive shaft 22 and the bone screw 100. In the illustrated embodiment, the distal end portion 24 defines six axially-extending slots 74 that correspondingly divide the distal end portion 24 into a six individual fingers or arms 80, with the fingers 80 being inwardly and outwardly deflected substantially independent of one another. However, it should be understood that the distal end portion 24 may define any number axially extending slots 74 that divide the distal end portion into a corresponding number of individual arms 80.

The axial passage 70 includes a recessed receiver portion 82 adjacent the distal end 72 of the drive shaft 22 that is sized and configured to receive the head portion 104 of the bone screw 100 therein to selectively and releasably engage the bone screw 100 to the distal end portion 24 of the drive shaft 22. In the illustrated embodiment of the invention, the receiver portion 82 has a size and shape corresponding to that of the head portion 104 of the bone screw 100. Specifically, the receiver portion 82 is sized and shaped to receive a splined head or stem therein, such as, for example, the Torx™ style head portion 104 of the bone screw 100. As shown most clearly in FIG. 5, the receiver portion 82 includes a number of transverse recessed areas 84 which are sized and configured to receive the projections 120 extending radially outward from the screw head portion 104. In the illustrated embodiment, the recessed areas 84 are generally aligned with the axial slots 74. However, it should be understood that in other embodiments, the recessed areas 84 may be positioned intermediate or offset from the axial slots 74. The recessed areas 84 preferably have an axial depth d (FIG. 7) that is substantially equal to the depth of the screw head portion 104 such that the screw head portion 104 is entirely received within the receiver portion 82 of the axial passage 70 (FIG. 8). The recessed areas 84 also define distally-facing shoulders 86 against which the screw head projections 120 are engaged to prevent the bone screw 100 from being positioned too far into the axial passage 70.

As shown in FIG. 5, the regions intermediate the recessed areas 84 define inwardly extending transverse protrusions 90. In a further aspect of the invention, the transverse protrusions 90 have distally-facing surfaces 92 which are taper cut or chamfered in an outward direction relative to the longitudinal axis L at a taper angle α (FIG. 7). In one embodiment of the invention, the taper angle a is approximately 50 degrees. However, other taper angles α are also contemplated, including taper angles greater than 50 degrees or less than 50 degrees. In the illustrated embodiment of the invention, the tapered surfaces 92 open onto the distal end 72 of the drive shaft 22. However, it should be understood that the tapered surfaces 92 need not necessarily open onto the distal end 72. Additionally, although the tapered surfaces 92 are illustrated as having a generally flat or planar configuration, it should be understood that the tapered surfaces 92 may alternatively take on a curved or arcuate configuration. Further, although the points of intersection between the tapered surfaces 92 and the axially-extending surfaces 94 of the transverse protrusions 90 are illustrated as defining relatively sharp edges 96, it should be understood that the edges 96 may be chamfered or rounded. Additionally, the distal end 72 of the drive shaft 22 is provided with an outer chamfer 98 to minimize trauma or injury to adjacent tissue. Alternatively, the distal end 72 may be rounded to minimize trauma or injury to adjacent tissue.

Referring to FIG. 8, shown therein is the bone screw 100 engaged to the distal end portion 24 of the drive shaft 22. Specifically, the head portion 104 of the bone screw 100 is positioned within the receiver portion 82 of the axial passage 70 defined by the drive shaft 22, with the Torx™ style transverse projections 120 positioned within the transverse recessed areas 84. The inner profile of the receiver portion 82 is preferably sized somewhat smaller than the outer profile of the screw head portion 104 such that insertion of the screw head portion 104 into the receiver portion 82 slightly deflects the flexible arms 80 in an outward direction. The resilient nature of the arms 80 results in compression of the arms 80 about the screw head portion 104. The resulting grip or frictional interference fit between the arms 80 and the screw head portion 104 maintains engagement between the drive shaft 22 and the bone screw 100.

Referring to FIG. 9, with the bone screw 100 selectively and releasably engaged within the receiver portion 82 of the drive shaft 22, the threaded shank portion 102 of the bone screw 100 is driven into bone. In the illustrated embodiment of the invention, the bone screw 100 is used to attach a spinal plate 200 to a vertebra V. Specifically, the plate 200 includes a number of openings 202 extending therethrough which are sized and shaped to receive the threaded shank portion 102 of the bone screw 100. The openings 202 may define internal threads adapted for threading engagement with the shank portion 102 of the bone screw 100, or may be unthreaded. In the illustrated embodiment, the upper portion of the plate opening 202 is tapered or countersunk so as to define a conically-shaped recess 204 opening onto an upper surface 206 of the plate 200. The conically-shaped recess is sized and shaped to at least partially receive the lower portion of the bone screw head 104 therein, with the lower tapered surface 126 of the bone screw 100 engaged in abutment against the upwardly facing tapered surface of the conically-shaped recess 204 when the bone screw 100 is fully seated within the plate opening 202. However, in other embodiments of the invention, the recess 204 may take on other configurations, such as, for example, a spherical configuration adapted to receive a spherical-shaped portion of a screw head therein, a cylindrical configuration adapted to receive a cylindrical-shaped portion of a screw head therein, or any other configuration that would occur to one of ordinary skill in the art.

As should be appreciated, to facilitate driving of the bone screw 100 into the vertebra V, the surgeon applies a torsional or rotational force onto the handle 28 in the direction of arrow R, which is in turn transmitted through the outer sleeve 26 and on to the drive shaft 22 via rotational engagement between the proximal passage portion 40 of the outer sleeve 26 and the proximal shaft portion 50 of the drive shaft 22. Rotation of the drive shaft 22 about the longitudinal axis L correspondingly drives the threaded shank portion 102 of the bone screw 100 into bone via rotational engagement of the inwardly extending protrusions 90 in the receiver portion 82 onto the outward projections 120 of the screw head portion 104. As should also be appreciated, to facilitate driving of the bone screw 100 into the vertebra V, the surgeon also applies an axial force $F_1$ onto the handle 28, which is in turn transmitted to the coil spring 68 via engagement of the distally-facing shoulder 46 of the outer sleeve 26 onto the proximal-most coil $68_p$. As should be further appreciated, exertion of an axial force $F_1$ onto the handle 28 to drive the bone screw 100 into the vertebra V will compress the coil spring 68 between the distally-facing shoulder 46 of the outer sleeve 26 and the upper drive shaft bearing 60a. As indicated above, the amount of axial force y generated by the compressed coil spring 68 is equal to the spring constant k multiplied by the distance x that the spring is compressed (i.e., $y_{lbs}=k*x_{in}$), with the axial force y generated by the compressed coil spring 68 being transmitted to the drive shaft 22 as an axial force $F_2$, which is in turn exerted onto the bone screw 100.

As should be appreciated, exertion of the axial force $F_1$ onto the handle 28 results in axial displacement of the outer sleeve 26 in the direction of arrow A. Since the proximal passage portion 40 and proximal shaft portion 50 are configured to permit relative axial displacement therebetween, axial displacement of the outer sleeve 26 does not require corresponding axial displacement of the drive shaft 22 in the direction of arrow A. Instead, the proximal shaft portion 50 is relatively displaced through the proximal passage portion 40. Notably, so long as the distal end 34 of the outer sleeve 26 is not positioned in abutment against the upper surface 206 of the plate 200 or against another rigid structure or substrate, the axial force $F_2$ exerted onto the bone screw 100 will be equal to the axial force $F_1$ exerted by the surgeon onto the handle 28.

However, as shown in FIG. 10, once the distal end 34 of the outer sleeve 26 is positioned in abutment against the upper surface 206 of the plate 200, the axial force $F_2$ exerted onto the bone screw 100 by the drive shaft 22 will be limited to the axial force y generated by the compressed coil spring 68. In other words, regardless of how much axial force $F_1$ the surgeon exerts onto the handle 28, once the distal end 34 of the outer sleeve 26 is engaged against the upper surface 206 of the plate 200, the axial force $F_2$ transmitted to the drive shaft 22 will be limited to the amount of axial force y transmitted through the compressed coil spring 68. Accordingly, the axial force $F_2$ transmitted to the drive shaft 22 by the compressed coil spring 68 and onto the bone screw 100 is equal to the spring constant k multiplied by the distance x that the outer sleeve 26 is displaced between the initial position illustrated in FIG. 9 and the fully displaced position illustrated in FIG. 10 (i.e., $y_{lbs}=k*x_{in}$). As will be discussed below, limiting or regulating the axial force $F_2$ applied to the head portion 104 of the bone screw 100 facilitates disengagement of the distal end portion 24 of the drive shaft 22 from the screw head portion 104 once a predetermined level or torque is applied to the screw head 104. Additionally, limiting or regulating the axial force $F_2$ applied to the drive shaft 22 reduces the risk of breaking or bending the drive shaft 22.

As shown in FIG. 10, once the head portion 104 of the bone screw 100 is fully seated within the recess 204 in the bone plate 200 (i.e., when the bone screw 100 can not be driven any further into the vertebra V), the distal end 72 of the drive shaft 22 will be positioned in abutment against the upper surface 206 of the bone plate 200. At this point, further rotational displacement of the drive shaft 22 will cause the inward protrusions 90 in the receiver portion 82 to rotationally ride up onto the projections 120 of the screw head portion 104, which will in turn outwardly deflect the axial arms 80 to disengage the drive shaft 22 from the bone screw 100. As should be appreciated, the controlled disengagement between the distal end portion 24 of the drive shaft 22 and the head portion 104 of the bone screw 100 limits the amount of torque applied to the bone screw 100, thereby significantly reducing the risks associated with screw breakage resulting from the application of excessive torque onto the bone screw 100. Moreover, limiting the amount of torque applied to the bone screw 100 may also reduce the likelihood of stripping out the threads formed in the bone.

Additionally, as the inward protrusions 90 in the receiver portion 82 ride up onto the projections 120 of the screw head portion 104, the distally-facing tapered surfaces 92 defined by the protrusions 90 further facilitate disengagement of the drive shaft 22 from the bone screw 100 by allowing the protrusions 90 to slide over and along the projections 120, which in turn allows the distal end portion 24 of the drive shaft 22 to "walk off" the screw head portion 104. Moreover, since the drive shaft 22 is allowed to be displaced in an axial direction relative to the outer sleeve 26, as the inward protrusions 90 in the receiver portion 82 ride up onto and slide along the projections 120 of the screw head 104, the drive shaft 22 will be axially displaced or "backed out" in the direction of arrow B (i.e., toward the handle 28) to further facilitate disengagement of the drive shaft 22 from the screw head 104 to thereby limit or regulate the amount of torque applied to the bone screw 100.

As indicated above, limiting the amount of torque applied to the bone screw 100 reduces the risk of breaking or shearing of the bone screw 100 and/or stripping out the threads formed in the bone. In one embodiment, the driver instrument 20 is configured to disengage the head portion 104 of the bone screw 100 at a point just before application of additional torque to the screw head portion 104 would result in the breaking or shearing of the bone screw 100 due to the buildup of excessive torque and/or stripping of the threads formed in the bone. However, in other embodiments, the driver instrument 20 may be configured to disengage the head portion 104 of the bone screw 100 well before the point at which application of additional torque would result in the breaking or shearing of the bone screw 100 and/or stripping of the threads formed in the bone.

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected.

What is claimed is:

1. A surgical instrument for driving a threaded member into a substrate, comprising:

a drive shaft extending generally along a longitudinal axis and including a distal end portion releasably and rotationally engaged with the threaded member;

a support member including a distal end positioned adjacent said distal end portion of said drive shaft, said drive shaft axially coupled with said support member to allow relative axial displacement therebetween, said drive shaft rotatably coupled with said support member by features that substantially prevent rotational displacement therebetween while allowing said relative axial displacement such that a rotational force applied to said support member is transmitted through said drive shaft to the threaded member, said features comprising a transverse projection positioned within an axially-extending groove, wherein said drive shaft includes an axially-extending shaft portion having a non-circular outer cross-section taken in a plane perpendicular to said longitudinal axis and positioned within an axially-extending passage portion defined by said support member; and a biasing member engaged with portions of said support member and said drive shaft to transmit an axial force from said support member to said drive shaft, said biasing member exerting an axial biasing force onto said drive shaft in a distal direction which is transmitted through said drive shaft to the threaded member as the threaded member is driven into the substrate, said axial force being limited as said distal end of said support member is engaged against a surface adjacent the substrate to correspondingly limit an axial force exerted onto the threaded member by said drive shaft to said axial biasing force to facilitate rotational disengagement of said distal end portion of said drive shaft from the threaded member.

2. The surgical instrument of claim 1, wherein said distal end portion of said drive shaft includes a distal end and a passage extending from said distal end generally along said longitudinal axis, said passage being sized and shaped to receive a head portion of the threaded member therein.

3. The surgical instrument of claim 1, wherein said axial force exerted onto the threaded member by the drive shaft is limited to the amount of force transmitted through said biasing member and onto said drive shaft when said distal end of said support member is engaged against the surface adjacent the substrate.

4. The surgical instrument of claim 3, wherein said biasing member comprises a coil spring.

5. The surgical instrument of claim 1, wherein said support member comprises an outer sleeve defining an axial passage sized to receive said drive shaft therein, the surgical instrument further comprising a handle extending from said outer sleeve.

6. The surgical instrument of claim 1, wherein said biasing member comprises a coil spring.

7. The surgical instrument of claim 1, wherein the threaded member comprises a bone screw.

8. The surgical instrument of claim 7, wherein said bone screw is formed of a polymeric material.

9. The surgical instrument of claim 1, wherein the threaded member comprises a bone tap.

10. The surgical instrument of claim 1, wherein said axially-extending passage portion defined by said support member has a non-circular inner cross section.

11. The surgical instrument of claim 10, wherein said non-circular outer cross section of said axially-extending shaft portion has a first shape and said non-circular inner cross section of said axially-extending passage portion has a second shape corresponding to said first shape.

12. The surgical instrument of claim 1, wherein said axially-extending shaft portion includes a number of flatted areas defining said non-circular outer cross section.

13. The surgical instrument of claim 12, wherein said non-circular outer cross section of said axially-extending shaft portion has a generally triangular-shaped configuration.

14. A surgical instrument for driving a threaded member into a substrate, comprising:

a drive shaft extending generally along a longitudinal axis and including a distal end portion releasably and rotationally engaged with the threaded member, wherein said distal end portion of said drive shaft includes a distal end and a passage extending from said distal end generally along said longitudinal axis, said passage being sized and shaped to receive a head portion of the threaded member therein, wherein said passage defines one or more tapered regions tapering outwardly toward said distal end to facilitate rotational disengagement of said drive shaft from the head portion of the threaded member;

a support member including a distal end positioned adjacent said distal end portion of said drive shaft, said drive shaft axially coupled with said support member to allow relative axial displacement therebetween, said drive shaft rotatably coupled with said support member by features that substantially prevent rotational displacement therebetween while allowing said relative axial displacement such that a rotational force applied to said support member is transmitted through said drive shaft to the threaded member, said features comprising a transverse projection positioned within an axially extending groove; and a biasing member engaged with portions of said support member and said drive shaft to transmit an axial force from said support member to said drive shaft, said biasing member exerting an axial biasing force onto said drive shaft in a distal direction which is transmitted through said drive shaft to the threaded member as the threaded member is driven into the substrate, said axial force being limited as said distal end of said support member is engaged against a surface adjacent the substrate to correspondingly limit an axial force exerted onto the threaded member by said drive shaft to said axial biasing force to facilitate rotational disengagement of said distal end portion of said drive shaft from the threaded member.

15. The surgical instrument of claim 14, wherein said tapered regions open onto said distal end of said drive shaft.

16. The surgical instrument of claim 14, wherein said tapered regions cause said distal end of said drive shaft to walk off of the head portion of the threaded member upon application of a select amount of torque to said drive shaft.

17. A surgical instrument for driving a threaded member into a substrate, comprising:

a drive shaft extending generally alone a longitudinal axis and including a distal end portion releasably and rotationally engaged with the threaded member, wherein said distal end portion of said drive shaft includes a distal end and a passage extending from said distal end generally along said longitudinal axis, said passage being sized and shaped to receive a head portion of the threaded member therein, wherein said distal end portion of said drive shaft defines one or more slots extending from said distal end generally along said longitudinal axis to facilitate flexible outward expansion of said distal end portion to releasably engage the head portion of the threaded member within said passage;

a support member including a distal end positioned adjacent said distal end portion of said drive shaft, said drive shaft axially coupled with said support member to allow relative axial displacement therebetween, said drive shaft rotatably coupled with said support member by features that substantially prevent rotational displacement therebetween while allowing said relative axial displacement such that a rotational force applied to said support member is transmitted through said drive shaft to the threaded member, said features comprising a transverse projection positioned within an axially extending groove; and a biasing member engaged with portions of said support member and said drive shaft to transmit an axial force from said support member to said drive shaft, said biasing member exerting an axial biasing force onto said drive shaft in a distal direction which is transmitted through said drive shaft to the threaded member as the threaded member is driven into the substrate, said axial force being limited as said distal end of said support member is engaged against a surface adjacent the substrate to correspondingly limit an axial force exerted onto the threaded member by said drive shaft to said axial biasing force to facilitate rotational disengagement of said distal end portion of said drive shaft from the threaded member.

18. The surgical instrument of claim 17, wherein said distal end portion of said drive shaft defines two or more of said slots extending from said distal end generally along said longitudinal axis.

19. A surgical instrument for driving a threaded member into a substrate, comprising:

a drive shaft extending generally alone a longitudinal axis and including a distal end portion releasably and rotationally engaged with the threaded member, wherein said distal end portion of said drive shaft includes a distal end and a passage extending from said distal end generally along said longitudinal axis, said passage being sized and shaped to receive a head portion of the threaded member therein, wherein said passage includes a receiver portion extending from said distal end generally along said longitudinal axis, said receiver portion including one or more transversely extending recessed areas sized and shaped to receive a corresponding number of transverse projections extending from the head portion of the threaded member;

a support member including a distal end positioned adjacent said distal end portion of said drive shaft, said drive shaft axially coupled with said support member to allow relative axial displacement therebetween, said drive shaft rotatably coupled with said support member by features that substantially prevent rotational displacement therebetween while allowing said relative axial displacement such that a rotational force applied to said support member is transmitted through said drive shaft to the threaded member, said features comprising a transverse projection positioned within an axially extending groove; and a biasing member engaged with portions of said support member and said drive shaft to transmit an axial force from said support member to said drive shaft, said biasing member exerting an axial biasing force onto said drive shaft in a distal direction which is transmitted through said drive shaft to the threaded member as the threaded member is driven into the substrate, said axial force being limited as said distal end of said support member is engaged against a surface adjacent the substrate to correspondingly limit an axial force exerted onto the threaded member by said drive shaft to said axial biasing force to facilitate rotational disengagement of said distal end portion of said drive shaft from the threaded member.

20. The surgical instrument of claim 19, wherein said receiver portion of said passage and the head portion of the threaded member each have a splined configuration.

21. The surgical instrument of claim 19, wherein said distal end portion of said drive shaft defines one or more slots extending from said distal end generally along said longitudinal axis to facilitate flexible outward expansion of said distal end portion to releasably engage the head portion of the threaded member within said receiver portion of said passage, said slots being generally aligned with said recessed areas.

22. The surgical instrument of claim 19, wherein said receiver portion of said passage defines one or more tapered regions tapering outwardly toward said distal end to facilitate rotational disengagement of said drive shaft from the head portion of the threaded member, said tapered regions being positioned intermediate said recessed areas.

23. A surgical instrument for driving a threaded member into a substrate, comprising:

a drive shaft extending generally along a longitudinal axis and including a distal end portion having a distal end and defining a first axial passage extending from said distal end, said first axial passage being sized and shaped to receive a head portion of the threaded member therein with said distal end portion releasably and rotationally engaged with the threaded member;

an outer sleeve defining a second axial passage sized to receive said drive shaft therein and including a distal end positioned adjacent said distal end portion of said drive shaft, said drive shaft coupled with said outer sleeve to allow relative axial displacement of said drive shaft along said second axial passage, said drive shaft rotatably coupled with said outer sleeve by features that substantially prevent rotational displacement therebetween while allowing said relative axial displacement such that a rotational force applied to said outer sleeve is transmitted through said drive shaft to the threaded member, said features comprising a transverse projection positioned within an axially-extending groove, wherein said drive shaft includes an axially-extending shaft portion having a non-circular outer cross-section taken in a plane perpendicular to said longitudinal axis and positioned within an axially-extending passage portion defined by said outer sleeve; and a biasing member engaged with portions of said outer sleeve and said drive shaft to transmit an axial force from said outer sleeve to said drive shaft, said biasing member exerting an axial biasing force onto said drive shaft in a distal direction which is transmitted through said drive shaft to the threaded member as the threaded member is driven into the substrate, said axial force being limited as said distal end of said outer sleeve is engaged against a surface adjacent the substrate to correspondingly limit an axial force exerted onto the threaded member by said drive shaft to said axial biasing force to facilitate rotational disengagement of said distal end portion of said drive shaft from the head portion of the threaded member.

24. The surgical instrument of claim 23, wherein said axially-extending passage portion defined by said outer sleeve has a non-circular inner cross section.

25. The surgical instrument of claim 24, wherein said non-circular outer cross section of said axially-extending shaft portion has a first shape and said non-circular inner cross section of said axially-extending passage portion has a second shape corresponding to said first shape.

26. The surgical instrument of claim 23, wherein said axially-extending shaft portion includes a number of flatted areas defining said non-circular outer cross section.

27. The surgical instrument of claim 26, wherein said noncircular outer cross section of said axially-extending shaft portion has a generally triangular-shaped configuration.

28. A surgical instrument for driving a threaded member into a substrate, comprising:
a drive shaft extending generally along a longitudinal axis and including a distal end portion having a distal end and defining a first axial passage extending from said distal end, said first axial passage being sized and shaped to receive a head portion of the threaded member therein with said distal end portion releasably and rotationally engaged with the threaded member, wherein said first axial passage defines one or more tapered regions tapering outwardly toward said distal end of said drive shaft to facilitate rotational disengagement of said distal end portion of said drive shaft from the head portion of the threaded member;
an outer sleeve defining a second axial passage sized to receive said drive shaft therein and including a distal end positioned adjacent said distal end portion of said drive shaft, said drive shaft coupled with said outer sleeve to allow relative axial displacement of said drive shaft along said second axial passage, said drive shaft rotatably coupled with said outer sleeve by features that substantially prevent rotational displacement therebetween while allowing said relative axial displacement such that a rotational force applied to said outer sleeve is transmitted through said drive shaft to the threaded member, said features comprising a transverse projection positioned within an axially extending groove; and
a biasing member engaged with portions of said outer sleeve and said drive shaft to transmit an axial force from said outer sleeve to said drive shaft, said biasing member exerting an axial biasing force onto said drive shaft in a distal direction which is transmitted through said drive shaft to the threaded member as the threaded member is driven into the substrate, said axial force being limited as said distal end of said outer sleeve is engaged against a surface adjacent the substrate to correspondingly limit an axial force exerted onto the threaded member by said drive shaft to said axial biasing force to facilitate rotational disengagement of said distal end portion of said drive shaft from the head portion of the threaded member.

29. The surgical instrument of claim 28, wherein said tapered regions open onto said distal end of said drive shaft.

30. The surgical instrument of claim 28, wherein said tapered regions cause said distal end of said drive shaft to walk off of the head portion of the threaded member upon application of a select amount of torque to said drive shaft.

31. The surgical instrument of claim 28, wherein said one or more tapered regions include distally-facing surfaces tapering outwardly toward said distal end in a radial direction relative to said longitudinal axis to facilitate said rotational disengagement of said drive shaft from said head portion of the threaded member.

32. A surgical instrument for driving a threaded member into a substrate, comprising:
a drive shaft extending generally along a longitudinal axis and including a distal end portion having a distal end and defining a first axial passage extending from said distal end, said first axial passage being sized and shaped to receive a head portion of the threaded member therein with said distal end portion releasably and rotationally engaged with the threaded member, wherein said distal end portion of said drive shaft defines one or more slots extending from said distal end generally along said longitudinal axis to facilitate flexible outward expansion of said distal end portion to releasably engage the head portion of the threaded member within said first axial passage;
an outer sleeve defining a second axial passage sized to receive said drive shaft therein and including a distal end positioned adjacent said distal end portion of said drive shaft, said drive shaft coupled with said outer sleeve to allow relative axial displacement of said drive shaft along said second axial passage, said drive shaft rotatably coupled with said outer sleeve by features that substantially prevent rotational displacement therebetween while allowing said relative axial displacement such that a rotational force applied to said outer sleeve is transmitted through said drive shaft to the threaded member, said features comprising a transverse projection positioned within an axially extending groove; and
a biasing member engaged with portions of said outer sleeve and said drive shaft to transmit an axial force from said outer sleeve to said drive shaft, said biasing member exerting an axial biasing force onto said drive shaft in a distal direction which is transmitted through said drive shaft to the threaded member as the threaded member is driven into the substrate, said axial force being limited as said distal end of said outer sleeve is engaged against a surface adjacent the substrate to correspondingly limit an axial force exerted onto the threaded member by said drive shaft to said axial biasing force to facilitate rotational disengagement of said distal end portion of said drive shaft from the head portion of the threaded member.

33. A surgical instrument for driving a threaded member into a substrate, comprising:
a drive shaft extending generally along a longitudinal axis and including a distal end portion having a distal end and defining a first axial passage extending from said distal end, said first axial passage being sized and shaped to receive a head portion of the threaded member therein with said distal end portion releasably and rotationally engaged with the threaded member, wherein said first axial passage includes a receiver portion extending from said distal end generally along said longitudinal axis, said receiver portion including one or more transversely extending recessed areas sized and shaped to receive a corresponding number of transverse projections extending from the head portion of the threaded member;
an outer sleeve defining a second axial passage sized to receive said drive shaft therein and including a distal end positioned adjacent said distal end portion of said drive shaft, said drive shaft coupled with said outer sleeve to allow relative axial displacement of said drive shaft along said second axial passage, said drive shaft rotatably coupled with said outer sleeve by features that substantially prevent rotational displacement therebetween while allowing said relative axial displacement such that a rotational force applied to said outer sleeve is transmitted through said drive shaft to the threaded member, said features comprising a transverse projection positioned within an axially extending groove; and
a biasing member engaged with portions of said outer sleeve and said drive shaft to transmit an axial force from said outer sleeve to said drive shaft, said biasing member exerting an axial biasing force onto said drive shaft in a distal direction which is transmitted through said drive shaft to the threaded member as the threaded member is driven into the substrate, said axial force being limited as said distal end of said outer sleeve is engaged against a surface adjacent the substrate to correspondingly limit an axial force exerted onto the threaded member by said drive shaft to said axial biasing force to facilitate rotational disengagement of said distal end portion of said drive shaft from the head portion of the threaded member.

34. The surgical instrument of claim 33, wherein said receiver portion of said passage and the head portion of the threaded member each have a splined configuration.

35. The surgical instrument of claim 33, wherein said distal end portion of said drive shaft defines one or more slots extending from said distal end generally along said longitudinal axis to facilitate flexible outward expansion of said distal end portion to releasably engage the head portion of the threaded member within said receiver portion of said passage, said slots being generally aligned with said recessed areas.

36. The surgical instrument of claim 33, wherein said receiver portion of said passage defines one or more tapered regions tapering outwardly toward said distal end to facilitate rotational disengagement of said drive shaft from the head portion of the threaded member, said tapered regions being positioned intermediate said recessed areas.

* * * * *